US009504272B2

(12) United States Patent
Carder et al.

(10) Patent No.: US 9,504,272 B2
(45) Date of Patent: Nov. 29, 2016

(54) METHOD OF PROCESSING OATS TO ACHIEVE OATS WITH AN INCREASED AVENANTHRAMIDE CONTENT

(71) Applicant: The Quaker Oats Company, Chicago, IL (US)

(72) Inventors: Gary Carder, Barrington Hills, IL (US); Robert E. Chatel, Barrington, IL (US); YiFang Chu, Glenview, IL (US); Yongsoo Chung, Palatine, IL (US); Justin A. French, Frisco, TX (US); Ursula Vanesa Lay Ma, Chicago, IL (US); Marianne O'Shea, Chicago, IL (US); Bernardus Jan-Willem Van Klinken, Barrington, IL (US)

(73) Assignee: The Quaker Oats Company, Chicago, IL (US)

( * ) Notice: Subject to any disclaimer, the term of this patent is extended or adjusted under 35 U.S.C. 154(b) by 0 days.

(21) Appl. No.: 13/784,255

(22) Filed: Mar. 4, 2013

(65) Prior Publication Data

US 2013/0183405 A1 Jul. 18, 2013

Related U.S. Application Data

(63) Continuation-in-part of application No. 12/264,399, filed on Nov. 4, 2008, now Pat. No. 8,574,644.

(51) Int. Cl.
| | | |
|---|---|---|
| *A23L 1/105* | (2006.01) | |
| *A23L 2/02* | (2006.01) | |
| *A23L 2/52* | (2006.01) | |
| *A23G 9/42* | (2006.01) | |
| *A23L 1/00* | (2006.01) | |
| *A21D 6/00* | (2006.01) | |
| *A23L 1/10* | (2006.01) | |
| *A23C 9/13* | (2006.01) | |
| *A21D 13/04* | (2006.01) | |
| *A23L 1/308* | (2006.01) | |

(52) U.S. Cl.
CPC .............. *A23L 1/1055* (2013.01); *A21D 6/00* (2013.01); *A21D 6/003* (2013.01); *A21D 13/04* (2013.01); *A23C 9/1315* (2013.01); *A23G 9/42* (2013.01); *A23L 1/0005* (2013.01); *A23L 1/0076* (2013.01); *A23L 1/1041* (2013.01); *A23L 1/308* (2013.01); *A23L 2/02* (2013.01); *A23L 2/52* (2013.01); *C12Y 302/01001* (2013.01); *A23V 2002/00* (2013.01)

(58) Field of Classification Search
CPC . A23L 1/1041; A23L 1/1055; A23L 1/0076; A23L 1/105; A23L 1/10; A23L 1/16; A23L 1/185; A23L 1/238; A23L 1/1016; A23L 1/1025; A23L 1/095; A21D 6/006; A23V 2250/5034
USPC .................... 426/28, 18, 590, 622, 660, 618
See application file for complete search history.

(56) References Cited

U.S. PATENT DOCUMENTS

| | | | |
|---|---|---|---|
| 1,163,175 A | 12/1915 | Rullman | |
| 1,384,894 A | 7/1921 | Horlick | |
| 3,116,150 A | 12/1963 | Baker | |
| 3,317,402 A | 5/1967 | Smith | |
| 3,391,003 A | 7/1968 | Armstrong | |
| 3,494,769 A | 2/1970 | Tressler | |
| 3,579,352 A * | 5/1971 | Bookwalter | .................. 426/598 |
| 3,595,671 A | 7/1971 | Cooke | |
| 3,732,109 A | 5/1973 | Poat | |
| 3,851,085 A | 11/1974 | Rodgers | |
| 3,869,558 A | 3/1975 | Hampton | |
| 3,925,343 A | 12/1975 | Hampton | |
| 3,958,016 A | 5/1976 | Galle | |
| 4,028,468 A | 6/1977 | Hohner | |
| 4,038,427 A | 7/1977 | Martin | |
| 4,171,384 A | 10/1979 | Chwalek | |
| 4,266,027 A | 5/1981 | Muller | |
| 4,282,319 A | 8/1981 | Conrad | |
| 4,330,625 A | 5/1982 | Miller | |
| 4,377,602 A | 3/1983 | Conrad | |
| 4,431,674 A | 2/1984 | Fulger | |
| 4,435,429 A | 3/1984 | Burrows | |
| 4,435,430 A | 3/1984 | Fulger | |
| 4,438,150 A | 3/1984 | Gantwerker | |
| 4,439,460 A | 3/1984 | Tsau et al. | |
| 4,500,558 A | 2/1985 | Fulger | |
| 4,551,347 A | 11/1985 | Karwowski | |
| 4,613,507 A | 9/1986 | Fulger et al. | |

(Continued)

FOREIGN PATENT DOCUMENTS

| | | |
|---|---|---|
| AU | 1989045913 | 12/1989 |
| CA | 1045890 | 1/1979 |

(Continued)

OTHER PUBLICATIONS

Anonymous: "Goldkill Instant Barley Drink", XP002561728, URL:http://web.archive.org/web/20060303003347/goldkill.com/goldkili_instant.php>, retrieved from the Internet on Dec. 28, 2009, pp. 1-2, dated Mar. 3, 2006.
Anonymous: "Ovsena nahradka mlieka", XP002561727, URL:http://web.archive.org/web/20080420075151/http://www.aspsk.sk/ovsene_mlieko.htm>, retrieved from the Internet on Dec. 18, 2009, pp. 1-1, dated Apr. 20, 2008.
Gualberto, D.G. et al., Effect of extrusion processing on the soluble and insoluble fiber, and phytic acid contents of cereal brans, dated Sep. 28, 1997.

(Continued)

*Primary Examiner* — Hamid R Badr
(74) *Attorney, Agent, or Firm* — Brandon V. Zuniga; James R. Gourley; Carstens & Cahoon, LLP

(57) ABSTRACT

Producing soluble oat flour with an increased level of avenanthramides by using enzymes to precondition whole oat flour prior to extrusion.

27 Claims, 7 Drawing Sheets

(56) References Cited

U.S. PATENT DOCUMENTS

| | | |
|---|---|---|
| 4,656,040 A | 4/1987 | Fulger |
| 4,668,519 A | 5/1987 | Dartey |
| 4,692,340 A | 9/1987 | Grutte |
| 4,710,386 A | 12/1987 | Fulger |
| 4,777,056 A | 10/1988 | Buhler |
| 4,834,988 A | 5/1989 | Karwowski |
| 4,834,989 A | 5/1989 | Bolles |
| 4,886,665 A | 12/1989 | Kovacs |
| 4,996,063 A | 2/1991 | Inglett |
| 4,999,208 A | 3/1991 | Lengerich |
| 5,021,248 A | 6/1991 | Stark |
| 5,082,673 A | 1/1992 | Inglett |
| 5,106,634 A | 4/1992 | Thacker |
| 5,106,643 A | 4/1992 | Laufer |
| 5,145,698 A | 9/1992 | Cajigas |
| 5,225,219 A | 7/1993 | Inglett |
| 5,234,704 A | 8/1993 | Devine |
| 5,320,856 A | 6/1994 | Veronesi |
| 5,334,407 A | 8/1994 | Donnelly |
| 5,385,746 A | 1/1995 | De Almeida |
| 5,395,623 A | 3/1995 | Kovach |
| 5,407,694 A | 4/1995 | Devine |
| 5,458,893 A | 10/1995 | Smith |
| 5,476,675 A | 12/1995 | Lou |
| 5,490,997 A | 2/1996 | Devine |
| 5,523,109 A | 6/1996 | Hellweg |
| 5,554,402 A | 9/1996 | Smith |
| 5,571,334 A | 11/1996 | Dunn et al. |
| 5,656,317 A | 8/1997 | Smits |
| 5,686,123 A | 11/1997 | Lindahl |
| 5,744,187 A | 4/1998 | Gaynor |
| 5,846,786 A | 12/1998 | Senkeleski |
| 5,849,090 A | 12/1998 | Haralampu et al. |
| 5,863,590 A | 1/1999 | Alan |
| 5,888,548 A | 3/1999 | Wongsuragrai |
| 5,912,031 A | 6/1999 | Fitchett |
| 5,932,264 A | 8/1999 | Hurd |
| 5,981,237 A | 11/1999 | Meagher |
| 5,985,339 A | 11/1999 | Kamarei |
| 5,997,917 A | 12/1999 | Uchida et al. |
| 6,013,289 A | 1/2000 | Blank |
| 6,054,302 A | 4/2000 | Shi |
| 6,135,015 A | 10/2000 | Mendez |
| 6,168,821 B1 | 1/2001 | Castleberry |
| 6,190,708 B1 | 2/2001 | Triantafyllou |
| 6,210,722 B1 | 4/2001 | Wullschleger |
| 6,210,738 B1 | 4/2001 | Chen |
| 6,210,741 B1 | 4/2001 | Van Lengerich |
| 6,244,528 B1 | 6/2001 | Wallis |
| 6,287,621 B1 | 9/2001 | Lacourse |
| 6,287,626 B1 | 9/2001 | Fox |
| 6,451,369 B1 | 9/2002 | Triantafyllou |
| 6,482,459 B1 | 11/2002 | Anderson |
| 6,551,366 B1 | 4/2003 | D'Souza |
| 6,592,914 B1 | 7/2003 | Triantafyllou |
| 6,610,349 B1 | 8/2003 | Delrue et al. |
| 6,617,446 B1 | 9/2003 | Papadopoulos |
| 6,685,974 B2 | 2/2004 | Whalen |
| 6,720,022 B1 | 4/2004 | Arnaut |
| 6,723,358 B1 | 4/2004 | van Lengerich |
| 6,759,077 B1 | 7/2004 | Lewis |
| 6,797,307 B2 | 9/2004 | Malkki et al. |
| 7,030,092 B1 | 4/2006 | Levine |
| 7,160,564 B2 | 1/2007 | Oste |
| 7,244,457 B2 | 7/2007 | Racicot |
| 7,419,694 B2 | 9/2008 | Korolchuk |
| 7,425,344 B2 | 9/2008 | Korolchuk |
| 7,754,270 B2 | 7/2010 | Wuersch |
| 7,794,774 B2 | 9/2010 | Foster |
| 8,241,696 B2 | 8/2012 | Chung |
| 8,518,469 B2 | 8/2013 | MacDonald |
| 8,574,644 B2 | 11/2013 | Chatel |
| 8,591,970 B2 | 11/2013 | Chatel |
| 9,149,060 B2 | 10/2015 | Chatel |
| 2001/0002269 A1 | 5/2001 | Zhao |
| 2001/0022986 A1 | 9/2001 | Girsh |
| 2002/0127319 A1 | 9/2002 | Gare |
| 2002/0187224 A1 | 12/2002 | Haefliger |
| 2003/0170362 A1 | 9/2003 | Manning |
| 2004/0028797 A1 | 2/2004 | Squire |
| 2004/0140584 A1 | 7/2004 | Wang |
| 2004/0151805 A1 | 8/2004 | Gao |
| 2004/0156971 A1* | 8/2004 | Wuersch et al. ............ 426/591 |
| 2004/0258829 A1 | 12/2004 | Zheng |
| 2005/0064080 A1 | 3/2005 | Creighton |
| 2005/0089602 A1 | 4/2005 | Kvist et al. |
| 2005/0106216 A1 | 5/2005 | Maurer et al. |
| 2005/0181114 A1 | 8/2005 | Bruemmer |
| 2005/0191400 A1 | 9/2005 | Satyavolu et al. |
| 2005/0214347 A1 | 9/2005 | Astrup et al. |
| 2005/0238777 A1 | 10/2005 | Klingeberg et al. |
| 2005/0244563 A1 | 11/2005 | Cavalieri et al. |
| 2005/0260305 A1 | 11/2005 | Adele et al. |
| 2006/0008574 A1 | 1/2006 | Begli et al. |
| 2006/0013940 A1 | 1/2006 | Mueller |
| 2006/0093720 A1 | 5/2006 | Tatz |
| 2006/0115573 A1 | 6/2006 | Singer et al. |
| 2006/0121174 A1 | 6/2006 | Franke |
| 2006/0134299 A1 | 6/2006 | Lahteenmaki |
| 2006/0141097 A1 | 6/2006 | Guo |
| 2006/0240148 A1 | 10/2006 | Nguyen et al. |
| 2006/0251791 A1 | 11/2006 | Rubio |
| 2006/0257548 A1 | 11/2006 | Crofskey |
| 2006/0280838 A1 | 12/2006 | Kvist |
| 2006/0286269 A1 | 12/2006 | Shah |
| 2007/0014892 A1 | 1/2007 | Mitchell |
| 2007/0059340 A1 | 3/2007 | Bello |
| 2007/0104854 A1* | 5/2007 | Foster et al. ............... 426/620 |
| 2007/0141218 A1 | 6/2007 | Chatel |
| 2007/0154609 A1 | 7/2007 | Li |
| 2007/0172568 A1 | 7/2007 | Spelman |
| 2007/0178199 A1 | 8/2007 | Minor |
| 2007/0184175 A1 | 8/2007 | Rubio |
| 2007/0212472 A1 | 9/2007 | Holenstein |
| 2007/0243301 A1 | 10/2007 | Barnett |
| 2007/0264400 A1 | 11/2007 | Milne |
| 2007/0292583 A1 | 12/2007 | Haynes |
| 2008/0003340 A1 | 1/2008 | Karwowski |
| 2008/0008801 A1 | 1/2008 | Barnekow |
| 2008/0131582 A1 | 6/2008 | Karwowski |
| 2008/0171114 A1 | 7/2008 | Rodriguez |
| 2008/0260909 A1 | 10/2008 | Chung |
| 2008/0305212 A1 | 12/2008 | Wong |
| 2009/0053771 A1 | 2/2009 | Dale |
| 2009/0148562 A1 | 6/2009 | Lin |
| 2009/0181128 A1 | 7/2009 | Blumenthal |
| 2009/0238935 A1 | 9/2009 | Haynes |
| 2009/0311376 A1 | 12/2009 | Rao |
| 2010/0104718 A1 | 4/2010 | Durand |
| 2010/0112167 A1 | 5/2010 | Chatel |
| 2010/0316765 A1 | 12/2010 | French et al. |
| 2011/0020523 A1 | 1/2011 | Pereyra et al. |
| 2012/0082740 A1 | 4/2012 | Collins et al. |
| 2013/0017300 A1 | 1/2013 | Avila et al. |
| 2013/0183405 A1 | 7/2013 | Chatel et al. |
| 2013/0209610 A1 | 8/2013 | Carder et al. |
| 2014/0193563 A1 | 7/2014 | Carder |
| 2014/0196564 A1 | 7/2014 | Carder |
| 2015/0351432 A1 | 12/2015 | Triantafyllou |

FOREIGN PATENT DOCUMENTS

| | | |
|---|---|---|
| CN | 1386446 | 12/2002 |
| CN | 1499940 | 5/2004 |
| DE | 970141 | 8/1958 |
| EP | 0231729 | 8/1987 |
| EP | 0609169 | 8/1994 |
| EP | 0634106 | 1/1995 |
| EP | 0806434 | 11/1997 |
| EP | 0897673 | 2/1999 |
| EP | 1782699 | 5/2007 |
| EP | 2205101 | 5/2010 |
| FR | 2620906 | 3/1989 |
| GB | 1168692 | 10/1969 |

(56) References Cited

FOREIGN PATENT DOCUMENTS

| | | |
|---|---|---|
| JP | S63116657 | 5/1988 |
| JP | 2000004852 | 1/2000 |
| JP | 2002171920 | 6/2002 |
| RU | 2237419 | 10/2001 |
| WO | 9210106 | 6/1992 |
| WO | 9604799 | 2/1996 |
| WO | 0030457 | 6/2000 |
| WO | 02076244 | 10/2002 |
| WO | 03011052 | 2/2003 |
| WO | 03090557 | 11/2003 |
| WO | 2004086878 | 10/2004 |
| WO | 2006009169 | 1/2006 |
| WO | 2007020059 | 2/2007 |
| WO | 2008028994 | 3/2008 |
| WO | 2008096044 | 8/2008 |
| WO | 2009077659 | 6/2009 |
| WO | 2009109703 | 9/2009 |
| WO | 2009127687 | 10/2009 |

OTHER PUBLICATIONS

Gutkoski, L.C., et al., "Effect of Extrusion Process Variables on Physical and Chemical Properties of Extruded Oat Products", Plant Foods for Human Nutrition, © 2000 Kluwer Academic Publishers, pp. 315-325.
Inglett, G.E. et al. 1994. Oat beta-glucan-amylodextrin: Preliminary preparations and biological properties. plant Fd. for Human Nutrition. 45: 53-61.
Linko Y Y et al: The effect of HTST-extrusion on retention of cereal alpha-amylase activity and on enzymatic hydrolisis of barley starch, Food Processing Systems, Applied Science Publ, UK, Jan. 1, 1980, pages Abstr, 4.2.25, 210-223, XP009127925, ISBN: 978-0-85334-896-2.
PCT/US2009/060016, International Search Report, mailed Feb. 8, 2010.
Peter Koelln KGAA: "Kochjule, Hafer-Getrank mit Fruchtsaft", XP002499645, Internet Citation, URL:http://www.koelln.de/downloads/37/Kochjule.pdf>, retrieved from the Internet on Oct. 14, 2008, pp. 1-19, dated Oct. 14, 2008, copy unavailable.
Peter Kolln KGAA: "KollnFlocken Instant", XP002499437, Internet Citation, URL:http://www.koelln.de/produkte/1/15/index.html>, retrieved from the Internet on Oct. 13, 2008, p. 1, dated Oct. 13, 2008.
Peter Kolln KGAA: "Kolln Schmelzflocken Dinkel-Hafer", XP002499438, Internet Citation, URL:http://www.koelln.de/produkte/2/103/index.html>, retrieved from the Internet on Oct. 13, 2008, p. 1, dated Oct. 13, 2008.
Vasanthan, V. et al., "Dextrinization of Starch in Barley Flours With Thermostable Alpha-Amylase by Extrusion Cooking", Starke-Starch, Wiley-VCH Verlag, Weinheim, DE, XP001110714, ISSN: 0038-9056, vol. 53, No. 12, pp. 616-622, dated Dec. 1, 2001.
Wang Changquing, et al, Study on the Extruding Production Method of Soluble Oats Fiber, vol. 28, No. 2, pp. 45-48, dated Mar. 20, 2002, with English Abstract.
Wang, Ming-chun, et al, Extrusion Technology Applied in the Nutritional Health Foods, College of Food Engineering & Biologic Technology, Tianjin University of Science and Technology, Tianjin 300457, pp. 63-66, dated Aug. 1, 2007, with English Abstract.
Written Opinion and International Search Report for PCT Application No. PCT/US2010/038506 mailed Aug. 10, 2010, 18 pages.
Zhang Haodong, "Starch Article Technology", Jilin Science and Technology Press, dated Feb. 29, 2008—copy unavailable.
Australian Patent Application No. 2010260219 Office Action dated Aug. 23, 2012.
Chinese Patent Application No. 201080022395.5 Office Action dated Nov. 8, 2012.
Canadian Patent Application No. 2,761,566 Office Action dated Dec. 27, 2012.
Russian Patent Application No. 2011145771 Office Action dated Jan. 21, 2013.
Chinese Patent Application 200880025660.8, Office Action dated Aug. 2, 2012.
European Patent Application 09740225.9 Office Action dated May 16, 2011.
European Patent Application 09 740 225.9 Office Action dated Oct. 11, 2010.
Chinese Patent Application No. 200880025660.8, Office Action Mailed Apr. 11, 2013.
Chinese Patent Application No. 200880025660.8, Office Action Mailed Oct. 10, 2013.
EP Application No. 12188138.7 Office Action mailed Nov. 13, 2013.
Russian Application No. 2011145771 Office Action mailed Apr. 18, 2013.
Mexican Application No. Mx/a/2010/000255 Office Action mailed Aug. 29, 2013.
Malaysian Application No. PI20095590 Office Action mailed Apr. 15, 2014.
Australian Application No. 2009251225 Office Action mailed Mar. 28, 2014.
International Search Report and Written Opinion for PCT/US2014/17288 mailed Jun. 13, 2014.
International Search Report and Written Opinion for PCT/US2014/26367 dated Sep. 9, 2014.
Davis, "The Effect of Cold on Micro-Organisms in Relation to Dairying," Express Dairy Co (London), Proceedigns of the Society for Applied Bacteriology, vol. 14, Issue 2, pp. 216-242, Oct. 1951.
Food Reference, About.com "Why Does Milk Curdle," http://foodreference.about.com/od/Dairy/a/Why-Does-Milk-Curdle.htm, pp. 1-2.
PCT Application No. PCT/US2012/046450 ISR-WO mailed Sep. 6, 2012.
Springer New York, "Milk and Milk Products," Essentials of Food Science, Food Science Texts Series, pp. 237-26.
Anderson, et al. "Gelatinization of corn grits by roll cooking, extrusion cooking and steaming," Staerke 22:130-135.
Brenda, The comprehensive Enzyme Information System, BC 3.2.1.1.—alpha amylase; pp. 1 to 297; Retrieved from the internet: http://www.brenda-enzymes.info/php/result_flat.php4?ecno=3.2.1.1 &organism_list=, date unknown.
The Whole Grains Council, "What are the Health Benefits?," http://wholegrainscouncil.org/whole-grains-101/what-are-the-health-benefits, 2 pages.
Grenus, Food Product Design, Applications, Agglomerations, Jul. 20, 2014, Weeks Publishing Co., pp. 1-4, www.foodproductdesign.com/articles/2004/07/food-product-design-applications.
PCT Application No. PCT/US2008/060323 International Search Report and Written Opinion, dated Aug. 13, 2008.
PCT Application No. PCT/US2009/059916 International Search Report and Written Opinion, dated Feb. 16, 2010.
PCT Application No. PCT/US2014/021913 International Search Report and Written Opinion, dated Jun. 23, 2014.
Hoseney, R. Carl, "Principles of Cereal Science and Technology," 1986, American Association of Cereal Chemists, Inc., St. Paul, Minnesota 55121, pp. 148-149 (4 pages).

* cited by examiner

METHOD OF PROCESSING OATS TO ACHIEVE OATS WITH AN INCREASED AVENANTHRAMIDE CONTENT

REFERENCE TO RELATED APPLICATIONS

This application is a continuation-in-part of U.S. patent application Ser. No. 12/264,399 filed Nov. 4, 2008, the contents of which is expressly incorporated herein by reference in its entirety.

FIELD OF THE INVENTION

The present invention relates generally to whole oat flour having soluble components (hereinafter "soluble oat flour"). More specifically, the present invention relates to methods of making soluble oat flour with an increased avenanthramide content.

BACKGROUND OF THE INVENTION

Oatmeal has for many years been a staple of the human diet due to its health benefits. For example, numerous studies have shown that eating oatmeal on a daily basis can help lower blood cholesterol, reduce risk of heart disease, promote healthy blood flows as well as maintain healthy blood pressure levels. Additionally, oatmeal has a high content of complex carbohydrates and fibers, which facilitates slow digestion and stable blood-glucose levels.

Avenanthramides are antioxidants uniquely found in oats. Since their first isolation in the 1980's, more than 30 congeners have been characterized and the most abundant avenanthramides in oats are 2p, 2f and 2c. These polyphenols demonstrate potent antioxidant, anti-inflammatory and anti-atherosclerotic properties, and may be beneficial to people with chronic inflammatory diseases, allergy and cardiovascular disease. Beyond the food industry, avenanthramides' benefits have also been well documented. Tranilast, an analogue of avenanthramides, has been approved for treating inflammation-related disease and the skin care product Aveeno™ is based on the proven benefits of avenanthramides.

In order to achieve beneficial effects on human health, avenanthramides must be ingested in a sufficient amount. In a 1999 Tufts University study, avenanthramides were confirmed to be bioavailable and remain bioactive in humans after ingestion. After 60 or 120 mg consumption, the maximum concentrations of total plasma avenanthramide were 168 and 560 nM, respectively. A more recent study performed by the University of Minnesota showed that consumption of avenanthramides at doses as low as 0.4 or 9.2 mg/day for 8 weeks increased plasma total antioxidant activity and had dose-response effects on several antioxidant and anti-inflammatory parameters. These effects are probably due to the accumulation and high concentration of avenanthramides in different tissues and organs.

Avenanthramide content in oat grains varies based on cultivars and food processing methods. For example, heat treatment generally reduces avenanthramide 2f, 2c, and more profoundly 2p. The processing methods that increase avenanthramide content are of great importance to help people reach health benefits through regular consumption of oat products.

Nuclear factor-kappa B (NF-κB) is a family of eukaryotic nuclear transcription factors that regulate the transcription of DNA and are involved in the activation of genes related to inflammatory and immune responses. The regulation of the inflammatory response by NF-κB occurs via the enhancement of the expression of genes encoding proinflammatory cytokines, such as tumor necrosis factor (TNF)-α, interleukin (IL)-6, and interleukin (IL)-1β. Activation of NF-κB leads to inflammation that in turn is involved in the pathogenesis of many diseases, such as asthma, rheumatoid arthritis, and inflammatory bowel disease and is at least partially responsible for diseases such as atherosclerosis and Alzheimer's disease. Suppression of NF-κB, a regulator of the immune response to infection, is key in limiting the proliferation of cancer cells and reducing the level of inflammation. Studies have shown that avenanthramides inhibit NF-κB activation.

With today's hectic lifestyle, consumers are demanding convenience, such as portability and ease of preparation. Consumers desire oatmeal from a variety of food sources including beverages, and convenience foods such as bars, cookies, crackers, smoothies, and the like.

It is desired to prepare a whole oat product that has sufficient soluble fiber to meet the FDA threshold necessary to justify a health claim. For example, a whole oat product must have 0.75 g soluble beta-glucan fiber per serving of food. To prepare an oat beverage that contains at least 0.75 g soluble oat fiber per serving (about 18 g of whole grain oats), highly soluble oat flour must be used. Traditionally, highly soluble flour is prepared using enzymes such as α-amylase. The enzyme-treated oat flour is then drum or spray dried. This method takes place in at least two steps and is traditionally expensive and produces the soluble oat flour in low rates. For example, a slurry batch is prepared of flour (oat) and water (70-90% moisture content). Enzyme(s) are then added to the slurry and held at optimum enzyme reaction conditions followed by enzyme deactivation process. The slurry is then transferred into either a spray or drum drier.

A need exists in the field for oat flour that is highly dispersible in liquid or semisolid media, maintains its standard of identity as whole grain and is rich in antioxidants.

BRIEF SUMMARY OF THE INVENTION

Aspects of the invention relate to soluble oat flour having an increased avenanthramide content. The soluble oat flour product is whole oat flour and thus has characteristics of whole grain oats.

Aspects of the present invention relate to the use of the soluble oat flour in various beverages and food products in order to provide enhanced health benefits.

These and other aspects, along with advantages and features of the present invention herein disclosed, will become apparent through reference to the following description and the accompanying drawings. Furthermore, it is to be understood that the features of the various embodiments described herein are not mutually exclusive and can exist in various combinations and permutations.

DETAILED DESCRIPTION OF THE INVENTION

The present invention relates to soluble oat flour having an increased level of avenanthramides over soluble oat flour prepared in accordance with prior known methods. The soluble oat flour is prepared using an extruder or other suitable continuous cooker. The process is easier, less expensive, and less time-consuming than prior art processes.

Figure 4:
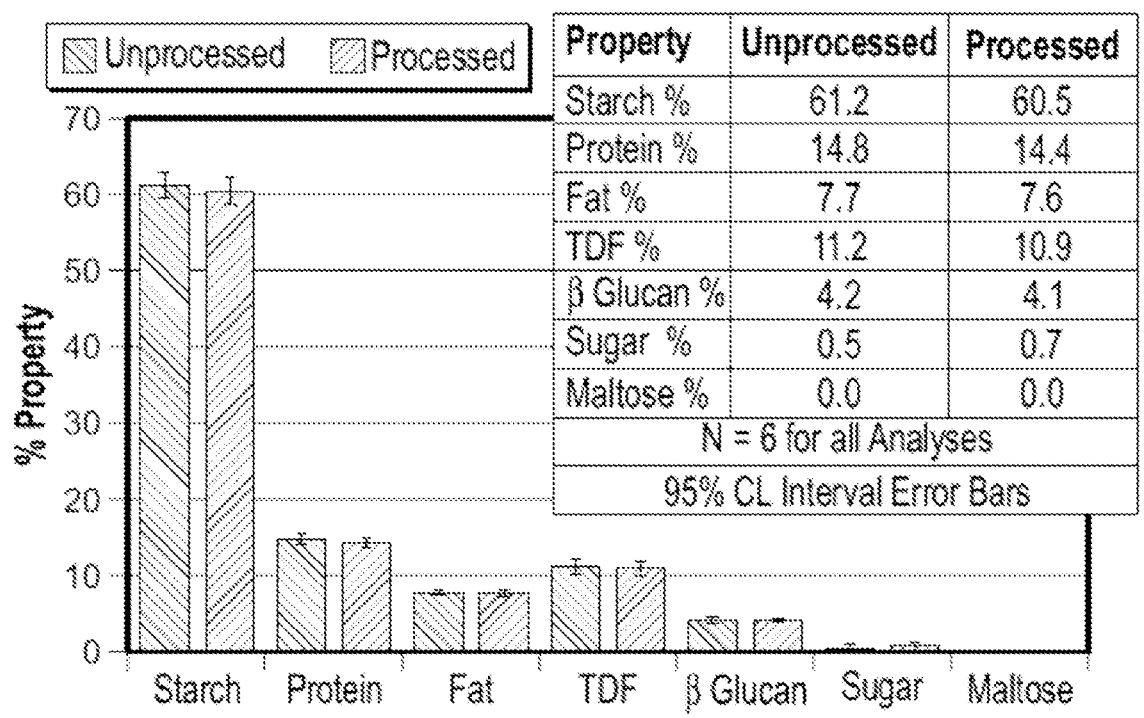
FIG. 4 depicts a proximate composition of unprocessed and processed whole oat flour.

The soluble whole oat flour made in accordance with the methods described herein maintains its standard of identity as whole grain throughout processing. "Whole grain" or "standard of identity as whole grain" shall mean that the cereal grain, in this instance, oat, "consists of the intact, ground cracked or flaked caryopsis, whole principal anatomical components—the starchy endosperm, germ and bran—are present in the same relative proportions as they exist in the intact caryopsis—should be considered a whole grain food." As shown in FIG. 4, the processed oat flour made in accordance with the instant disclosure maintains the same levels of starch, protein, fat, TDF, β glucan, sugar and maltose contain the same levels of the unprocessed oat flour.

The term "soluble oat flour" or "soluble whole grain oat flour" refers to flour that maintains soluble components such as beta-glucan but also is highly dispersible in liquids such as water. The dispersibility of the flour was measured in water observing formation of a lump and size of the lumps on the top and bottom of the water after stirring for five (5) seconds. "Highly dispersible" therefore means that there are no lumps present or formed after stirring the mixture for about 5 seconds. As the skilled artisan would recognize, stirring may also be substituted with shaking or some other specific movement to incorporate and mix the flour into the liquid.

Initially, enzyme-treated oat flour is prepared by combining a whole oat flour starting mixture and a suitable enzyme solution in a mixer (sometimes called a pre-conditioner) and then heating the mixture. The enzyme-treated mixture is then subjected to an extrusion process to hydrolyze, gelatinize, and cook the oat flour mixture.

A suitable starting mixture is prepared by combining the whole oat flour with other desired ingredients. For example, a typical starting mixture contains whole oat flour and granulated sugar. Maltodextrin and/or at least one antioxidant may also be added.

The whole oat flour is present in an amount of about 50% to about 100% by weight of the total weight of the starting composition. In further aspects, the whole oat flour is present in amounts of about 80% to about 95% by weight or about 90% to about 95% by weight.

The sugar can be any suitable sugar known to those skilled in the art. Non-limiting examples of sugars include sucrose, fructose, dextrose, other sugars known in the art, and combinations thereof. Typically, the sugar is present in an amount of about 1% to about 15% by weight or about 3% to about 15% by weight of the total weight of the starting composition. In further aspects, the sugar is present in amounts of about 3% to about 7% by weight.

The maltodextrin may be present in an amount of about 0% to about 15% by weight of the total weight of the starting composition. In further aspects, the maltodextrin is present in amounts of about 3% to about 7% by weight.

The antioxidant may be any suitable antioxidant such as mixed natural tocopherols or artificial antioxidant such as BHT and BHA. The antioxidant is present in an amount from 0.1% to 2% by weight. In further aspects, the antioxidant is present in amounts of about 0.25% to about 0.75% by weight.

A suitable flour mix formula for extrusion process.

| Ingredient | % |
| --- | --- |
| Whole oat flour | 89.35 |
| Sugar | 5.00 |
| Maltodextrin | 5.00 |
| Mixed tocopherols | 0.50 |
| α-amylase | 0.15 |
| Total | 100.00 |

The enzyme may be any suitable enzyme to hydrolyze the starch in the oat flour and does not change or adversely affect the beta-glucan that is present in the oat flour. Suitable enzymes include α-amylase in the range of about 0.01-0.5%, for example about 0.1-0.2%. In one aspect of the present disclosure, the α-amylase used may be Validase 1000 L having approximately 1,000,000 MWU/g (MWU—Modified Wohlgemuth Unit). Whether the beta-glucan has changed by the hydrolysis can be determined by any suitable method such as by analyzing the structure of the beta-glucan. This can be done by laser light scattering mass spectroscopy. The enzyme is added to water to form an enzyme water solution. Then the enzyme-water solution is combined with the starting mixture in the pre-conditioner.

The starting mixture and enzyme solution is heated to between about 120° F. and about 200° F., in particular to between about 140° F. and about 180° F., e.g. 165° F. for about 3 to 5 minutes to initiate gelatinization of starch. The enzyme then reacts on gelatinized starched to break down some of the high molecular weight amylopectin starch fractions (having an average molecular weight of $5.8-6.2 \times 10^6$ Dalton) into low molecular weight amylopectin starch fractions (having an average molecular weight of $1.7-2.0 \times 10^6$ Dalton).

The starting mixture and enzyme solution may be mixed in any suitable vessel such as a high speed mixer that permits liquid to be added to free-flowing flour. The output is a free-flowing wetted flour mixture having a moisture content of about 25 to about 40%. The residence time is the time sufficient to obtain the desired result and typically 1 to 5 min.

The enzyme-treated mixture is subsequently added to an extruder (continuous cooker) to hydrolyze, gelatinize, and cook the starch. The mixture resides in the extruder for a time sufficient to gelatinize and cook the starch, but not long enough to dextrinize or otherwise modify the starch to void the whole grain aspect, generally at least 1 minute, typically, about 1 to about 1.5 minutes. Generally, the material is heated from an initial inlet temperature to a final exit temperature in order to provide the energy for starch gelatinization.

Starch gelatinization requires water and heat. The gelatinization temperature range for oats is 127° F. to 138° F. (53-59° C.). If the moisture is less than about 60% then higher temperatures are required.

Heat may be applied through the extruder barrel wall such as with a jacket around the barrel through which a hot medium like steam, water or oil is circulated, or electric heaters imbedded in the barrel. Typically the extrusion occurs at barrel temperatures between 140° F. and 350° F., for example between 175° F. and 340° F., more specifically about 180° F.-300° F.

Heat is also generated within the material by friction as it moves within the extruder by the dissipation of mechanical energy in the extruder, which is equal to the product of the viscosity and the shear rate square for a Newtonian fluid. Shear is controlled by the design of the extruder screw(s) and the screw speed. Viscosity is a function of starch structure, temperature, moisture content, fat content and shear. The temperature of the dough increases in the extruder to approximately 212° F. and 300° F.

Low shear is applied to the mixture in the extruder. As the enzyme has preconditioned the starch, high shear is not required for this process. High shear can dextrinize the starch reducing its molecular weight too much. It can also increase the dough temperature excessively, which can overcook it resulting in too much cooked grain flavor. It is noted that the barrel temperature and the dough temperature may be different.

The process balances limiting the dough temperature to avoid too much cooked grain flavor and to keep the enzyme active. The process is balanced such that the dough temperature rises to a sufficient temperature to deactivate the enzyme. Such temperatures are at least 280° F., generally 212° F. to 300° F. A low shear extrusion process is characterized relative to high shear extrusion by high moisture and a low shear screw design versus low moisture and a high shear screw design.

Any suitable extruder may be used including suitable single screw or twin screw extruders. Typical, but not limiting, screw speeds are 200-350 rpm.

The resulting product may be pelletized using a forming extruder and dried, typically to about 1.5 to about 10%, for example 6.5 to 8.5%, moisture content. The pellets may be granulated to a max 5% though a US 40 screen. The particle size of the resulting granulated product is about 10-500 microns, for instance, about 1-450 microns, more particularly about 30-420 microns.

Jet milling may be used to mill the pellets produced in accordance with aspects of the present disclosure. Jet milling creates ultrafine particles. In particular, jet milling reduces the particle size of the pelletized soluble oat flour to less than about 90 micron, for example, less than about 50 microns, such as about 46 microns. As one of ordinary skill in the art would recognize, alternative milling processes can be used to reduce the particle size or micronize the flour to, 0.5-50 microns, such as between 10 to 50 microns.

The resulting soluble oat flour includes beta glucan soluble fiber, such as beta-1,3-glucan, beta-1,6-glucan, or beta-1,4-glucan or mixtures thereof. In addition to beta glucan naturally present in the oats, beta glucan may also be added as approved by the FDA. In certain embodiments, the oat flour preferably contains at least about 3% to 5% or about 3.7% to 4% beta glucan. In certain embodiments, the oat flour containing liquid product contains 0.1% to about 1.5% beta glucan, or about 0.8% to 1.3% beta glucan. Other amounts of beta glucan are also useful.

Water absorption and water solubility index of the soluble oat flour were determined according to Anderson et al. (Anderson et al., A. J. 1970. *Gelatinization of corn grits by roll cooking, extrusion cooking and steaming*. Staerke 22:130-135). The sample has relatively high water absorption and water solubility index. The water solubility and water absorption index are significantly higher than 100% oat flour. This is due to starch gelatinization and enzyme effects during the manufacturing process of soluble oat flour.

When starch gelatinizes, the starch granules disperse and become more accessible for water. In addition α-amylase cleaves starch molecules and reduces the size of starch molecules, which makes the flour more soluble. The combination of gelatinization and enzyme effect leads to increased water absorption and solubility of SoluOats. As used herein "SoluOat," "SoluOat flour," "SoluOat 90" or "regular SoluOat," whether singular or plural, shall mean 90% whole oat flour 5% sugar, 4.5% maltodextrin and 0.5% mixed tocopherol made in accordance with the methods set forth in the present disclosure.

| Sample | WAI (g)* | WSI (%)** |
|---|---|---|
| SoluOats 1 | 4.57 | 19.73 |
| SoluOats 2 | 4.67 | 20.00 |
| Raw Oat flour | 2.32 | 4.40 |

*Water absorption index (WAI) is the weight of gel obtained per gram of sample.
**Water solubility index (WSI) percentage of soluble dry solid in the sample.

Native oat flour and SoluOat flour were added to water at 2%, 4% and 8% whole grain levels and flours were dispersed at different conditions described in the table below. Viscosity of the solution was measured using a Brookfield viscometer with specified spindle. All viscosity measurements in the table below are identified in cP.

| | Native Oat Flour | | | Solu Oats | | |
|---|---|---|---|---|---|---|
| Treatment | 2% | 4% | 8% | 2.22% | 4.44% | 8.89% |
| Disperse in water at 4° C.—Spindle# 2 | 4 | 4 | 4 | 4 | 4 | 20 |
| | 4 | 4 | 6 | 4 | 2 | 18 |
| Disperse in water at 20-25° C.—Spindle# 2 | 2 | 2 | 4 | 4 | 4 | 28 |
| | 4 | 4 | 4 | 2 | 4 | 28 |
| Disperse in boiling water—Spindle# 2 | 2 | 2 | 26 | 4 | 4 | 75 |
| | 2 | 4 | 29 | 2 | 8 | 75 |
| Disperse at room temperature, boil for 5 minutes, cool to 4° C.—Spindle#6 | 0 | 1150 | 17850 | 0 | 0 | 800 |
| | 0 | 1150 | 15200 | 0 | 0 | 600 |

The viscosities of solutions containing SoluOat at 4% and 8% were significantly reduced when compared with that of native oat flour for samples boiled for 5 min.

The granulated product may be used in beverages such as ready-to-drink beverages, fruit juices, dairy beverages, and carbonated soft drinks, and various food products such as bars, cereals, puddings, smoothies, floured beverages, cookies, crackers, and the like. The soluble oat flour can be also be used to make soft food products such as ice cream and soft yogurt. This list is not all-inclusive and one skilled in the art would recognize that the soluble oat flour may be added to other beverages and food products in accordance with the invention.

A beverage, for example, contains from about 1% to about 25% soluble oat flour and from about 70% to about 95% total water, typically about 75% to about 90% total water, based on weight of the total drinkable beverage. The balance can contain sweeteners, flavors, fruits and other materials as desired.

The water should be suitable for use in food. The total water may be provided in part or in whole from other parts of the drinkable food, especially if milk, juices, or other water containing components are used. For instance, the milk may be dairy (e.g. whole, 2%, 1%, or non-fat) or non-dairy (e.g. soy). The milk may also be produced from powdered milk and water.

The beverage may also include a fruit component. The fruit component can include fruit juice, yogurt containing fruit, fruit puree; fresh fruit, fruit preserves, fruit sorbet, fruit sherbet, dried fruit powder, and combinations thereof. Typically, the fruit component has particles sufficiently small that the component may be safely swallowed without chewing. The fruit component and/or an added acidulant can be adjusted to obtain a desired pH, for example a pH of less than about 4.6.

Food products may include cereals and ready-to-eat snack bars. A suitable amount of the granulated product is added to the food mixture.

Additional ingredients may be added to the beverage and food products. Such ingredients can include non-grain-based ingredients. For example, flavoring agents, coloring agents, sweeteners, salt, as well as vitamins and minerals can be included. In one embodiment of the invention, flavoring agents such as strawberry, chocolate or cinnamon flavor is added to enhance the taste of the product. Other fruit flavoring agents may also be useful to provide different tastes to the food product, for example, strawberry, mango, banana and mixtures thereof. Spices, in particular, cinnamon, can be used. In addition, any desired flavor or flavors can be used. Suitable sweeteners—artificial or natural can be added in the food product to provide a desired sweetness. For example, brown sugar, maple sugar or fruit sugar can be used. The non-grain based food component can be added in the range of about 10 to 75 wt % of the total weight of the product.

Other optional ingredients may include, but are not limited to, salt, hydrocolloids, polysaccharides, thickeners, caffeine, dairy, coffee solids, tea solids, herbs, nutraceutical compounds, electrolytes, vitamins, minerals, amino acids, preservatives, alcohol, colorants, emulsifiers, and oils as known in the art.

A cracker formula is typically made from whole wheat flour or wheat gluten. Instead the formula would be replaced with this soluble oat flour to improve nutritional benefits (heart health) as well as provide adequate strength to the dough be sheeted and cut into crackers. The formula would include:

| Ingredient | % |
|---|---|
| Modified corn starch | 10.00 |
| Oat flour, Hydrolyzed | 48.00 |
| Oat flakes, old fashioned | 17.00 |
| Brown sugar, free-flowing | 12.00 |
| Malt powder, Briess #10001 | 4.00 |
| Lecithin, powdered, Centrolex F | 2.00 |
| Sodium aluminum phosphate | 0.80 |
| Sodium bicarbonate | 0.70 |
| Salt, flour | 0.60 |
| Corn Oil, with TBHQ, ADM | 5.00 |
| Total | 100.00 |

A formula for oat ice cream would include, for example,

| Ingredient | % |
|---|---|
| 2% Milk | 87.0 |
| Oat flour, hydrolyzed | 6.5 |
| Sugar | 5.4 |
| Cocoa powder | 0.8 |
| Flavor | 0.2 |
| Modified starch | 0.1 |
| Total | 100.0 |

The oat flour made in accordance with the processes described herein contains an increased avenanthramide level compared to unprocessed oats or native oat flour. In particular, native oat flour contains about 0.0002-0.03% total avenanthramides. Avenanthramides are polyphenols found only in oats. Avenanthramides have been shown to have significant antioxidant activity and have been linked to many beneficial health activities due to their potent antioxidant activities. In vivo testing has shown that the antioxidant capacity for avenanthramides provides health benefits such as a reduced rate of LDL oxidation thus protecting against cancers and heart disease. The structure of avenanthramide 2c is shown below:

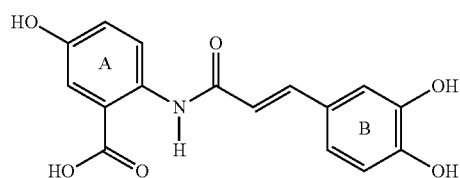

Applicants have found that the levels of the three main avenanthramides present in oat—2c, 2p and 2f—are all increased as a result of the processes described herein. In particular, the total avenanthramide level (including 2c, 2p and 2f) is elevated by about 20-35% compared to native whole oat flour by the methods used to prepare the soluble oat flour described above.

Example 1

Figure 1A:
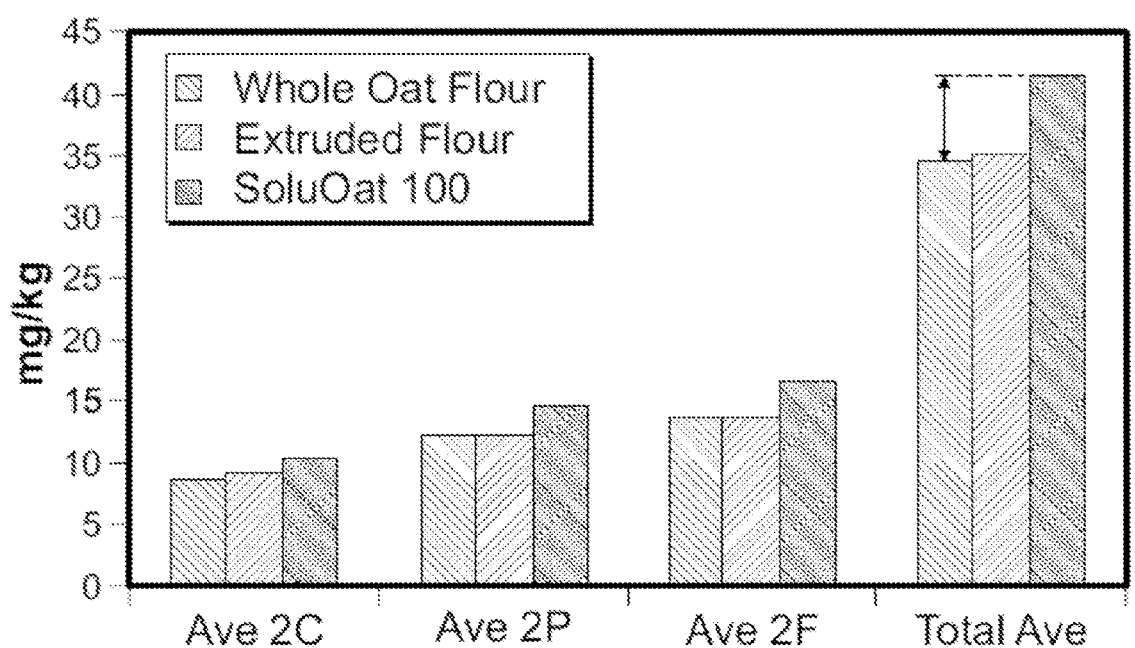
FIG. 1A compares the avenanthramide levels (2C, 2P, 2F and the total level of these avenanthramides) found in whole oat flour made using the methods described herein ("Solu-Oats").
Figure 1B:
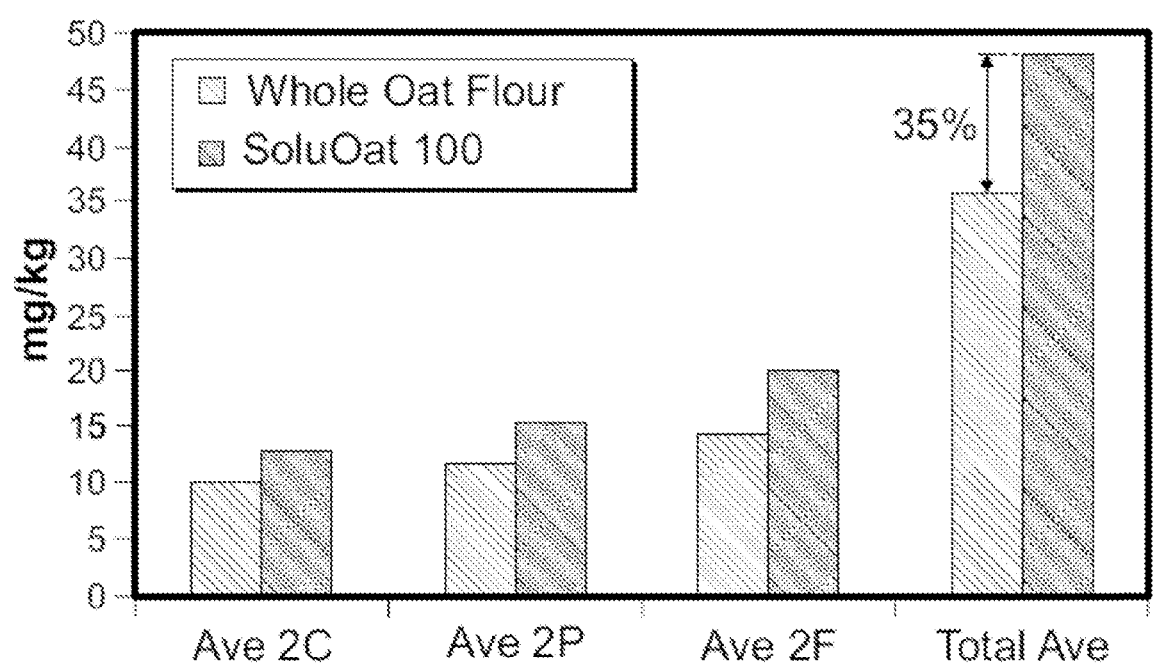
FIG. 1B compares the avenanthramide levels (2C, 2P, 2F and the total level of these avenanthramides) found in whole oat flour made using the methods described herein ("Solu-Oats").

The avenanthramide levels of the resulting soluble oat flour were measured using reverse-phase HPLC. Briefly dehulled grain was extracted, dried, and re-suspended into aliquots. Aliquots were analyzed by HPLC with a C-18 column using a diode array spectrophotometer detector with detection at 340 nm. The peaks were quantified by comparison to standard curves of authentic avenanthramides. The results of this testing are illustrated in FIG. 1A and FIG. 1B. The avenanthramide content of the soluble oat flour made in accordance with the methods described herein were also found to have higher avenanthramide content than oat flour processed using solely extrusion (no enzyme.)

In particular, FIG. 1A depicts the levels of avenanthramide 2c, avenanthramide 2p, avenanthramide 2f and the total avenanthramide (2c+2p+2f) in samples of native whole oat flour, extruded flour, and the SoluOat 100 flour made in accordance with the instant inventions. As used herein, "SoluOat 100," or "SoluOat 100 flour" whether singular or plural, shall mean 99.5% whole oat flour and 0.5% mixed tocopherol made in accordance with the methods set forth in the present disclosure.

As shown in FIG. 1A, the highest level of avenanthramides 2c, 2p and 2f, and the total avenanthramide content was found in the SoluOat 100 flour. In particular, the native whole oat flour was found to contain about 35 ppm total avenanthramides whereas the SoluOat 100 flour was found to contain over 40 ppm total avenanthramides resulting in a 20% increase in the level of avenanthramides in the SoluOat 100 flour compared to the native whole oat flour. In FIG. 1B a similar test was performed testing the avenanthramide content of native whole oat flour and the SoluOat 100 flour made in accordance with the instant invention. As shown in FIG. 1B, the native whole oat flour was found to have about 35 ppm of total avenanthramides whereas the SoluOat 100 flour contained about 45 ppm total avenanthramides. Thus, the SoluOat 100 flour exhibited a 35% increase in the level of total avenanthramides compared to the native whole oat flour.

The increased avenanthramide content of the soluble oat flour made via the embodiments described herein is surprising, since this antioxidant is a non-starch plant nutrient. However, the enzymatic process described above is used to improve dipsersibility and solubility of the flour.

Subsequent analysis was also performed to distinguish the amounts of the specific avenanthramides tested under various processing conditions and the levels of avenanthramides found following processing. The table below identifies the various process conditions tested:

| Process Condition | Extrusion | Enzyme Level | Moisture Level |
|---|---|---|---|
| 1 | No | 0% | Not controlled |
| 2 | Yes | 0% | 30% |
| 3 | Yes | Deactivated | 30% |
| 4 | Yes | 0.1% | 28% |
| 5 | Yes | 0.1% | 30% |
| 6 | Yes | 0.1% | 32% |
| 7 | Yes | 0.12% | 32% |
| 8 | Yes | 0.20% | 32% |

The table below identifies the avenanthramide level found in the oat flour under the different processing conditions along with the increase in avenanthramide content. All samples in the table that were extruded and hydrolyzed in accordance with the present disclosure are SoluOat 100, as defined above.

Figure 2:
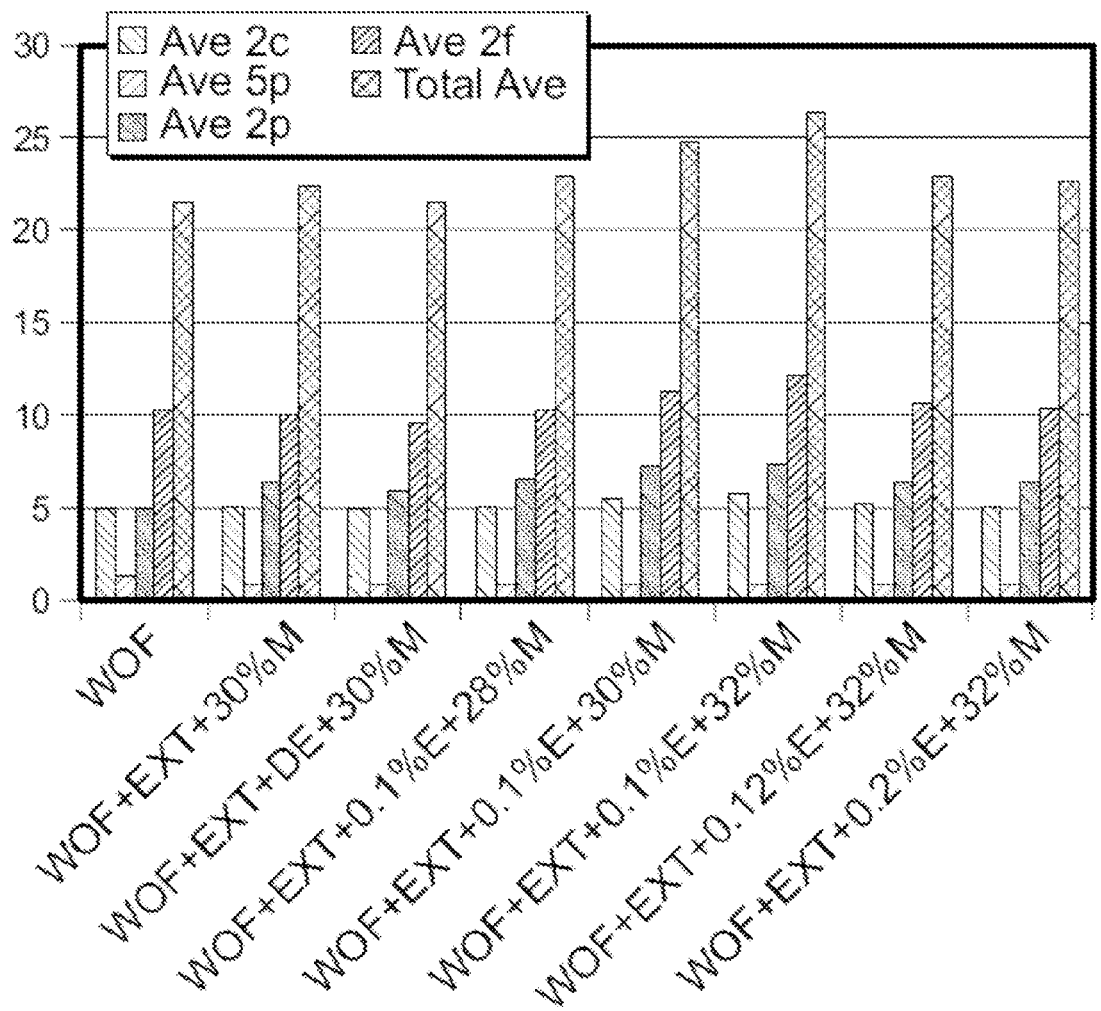
FIG. 2 compares the amount of avenanthramide identified in the oat flour as a result of the various processing conditions set forth in the table in paragraph [0064].

In accordance with the results shown in the above table as well as FIG. 2, Avenanthramide 2c has the highest antioxidant activity in vitro among the three major avenanthramides (2c, 2 p, 2f). With respect to in vivo activity, avenanthramide 2p has the highest bioavailability. Extrusion alone increased the total avenanthramide content slightly (3.72%), but dramatically increased avenanthramide 2p content (27.79%). Enzymatic digestion increased total and individual avenanthramide content, including that of 2c, 2p, and 2f. At a fixed enzyme concentration (0.1%), moisture levels of 28%, 30% and 32% increased the total avenanthramide content by 6.47%, 15.26%, and 22.47% respectively compared with the whole oat flour. Moisture content or moisture levels were measured when the mixture entered the extruder. At a fixed moisture level of 32%, enzyme concentrations of 0.12% and 0.20% did not increase avenanthramide content when compared to an enzyme concentration of 0.1%.

Furthermore, the soluble oat flour made in accordance with the instant methods also demonstrated an ability to suppress NF-κB. NF-κB is an immune response/inflammation trigger. In particular, reduced NF-κB is clinically linked to reduced chronic inflammation. Anti-inflammatory activity was measured by NF-κB inhibitory assay. Human 293T cells were cultured overnight in standard medium with fetal bovine serum and antibiotics followed by a 4-hour serum free to "starve" period. As one of ordinary skill in the art would recognize, "starved" cells are cells having a serum-free medium to eliminate the effects of fetal bovine serum and therefore the cells are more sensitive to TNF treatments. Afterward, cells were treated with TNF-α (100 ng/mL) and testing sample extracts for one hour at 37° C. with $CO_2$. Whole cell proteins were extracted and levels of NF-κB were measured using a TransAM NF-κB ELISA kit. The table below shows the results of the testing, comparing whole oat flour to SoluOats 90 and a blank. As used herein "SoluOat," "SoluOat flour," "SoluOat 90" or "regular SoluOat," whether singular or plural, shall mean 90% whole oat flour 5% sugar, 4.5% maltodextrin and 0.5% mixed tocopherol made in accordance with the methods set forth in the present disclosure.

|  | Ave 2c | Ave 5p | Ave 2p | Ave 2f | Total Ave |
|---|---|---|---|---|---|
|  | (mg/kg) | | | | |
| WOF | 5.01 | 1.24 | 4.93 | 10.32 | 21.50 |
| WOF + EXT | 5.13 | 0.87 | 6.3 | 10 | 22.30 |
| WOF + EXT + DE | 5 | 0.89 | 5.89 | 9.6 | 21.38 |
| WOF + EXT + 0.1% E + 28% M | 5.1 | 0.85 | 6.61 | 10.33 | 22.89 |
| WOF + EXT + 0.1% E + 30% M | 5.45 | 0.85 | 7.23 | 11.25 | 24.78 |
| WOF + EXT + 0.1% E + 32% M | 5.76 | 0.95 | 7.41 | 12.21 | 26.33 |
| WOF + EXT + 0.12%E + 32% M | 5.21 | 0.73 | 6.32 | 10.62 | 22.88 |
| WOF + EXT + 0.2% E + 32% M | 5.04 | 0.77 | 6.45 | 10.33 | 22.59 |
|  | Increase in Ave (%) | | | | |
| WOF | 0 | 0 | 0 | 0 | 0 |
| WOF + EXT | 2.40 | −29.84 | 27.79 | −3.10 | 3.72 |
| WOF + EXT + DE | −0.20 | −28.23 | 19.47 | −6.98 | −0.56 |
| WOF + EXT + 0.1% E + 28% M | 1.80 | −31.45 | 34.08 | 0.10 | 6.47 |
| WOF + EXT + 0.1% E + 30% M | 8.78 | −31.45 | 46.65 | 9.01 | 15.26 |
| WOF + EXT + 0.1% E + 32% M | 14.97 | −23.39 | 50.30 | 18.31 | 22.47 |
| WOF + EXT + 0.12% E + 32% M | 3.99 | −41.13 | 28.19 | 2.91 | 6.42 |
| WOF + EXT + 0.2% E + 32% M | 0.60 | −37.90 | 30.83 | 0.10 | 5.07 |

WOF: whole oat flour (unhydrolyzed); EXT: extrusion; E: Enzyme; DE: deactivated enzyme; M: moisture; Ave: avenanthramide

| Description | Yield of NF-κB† | % Inhibition* |
|---|---|---|
| Whole Oat Flour, Flour | 170 | Not detected |
| SoluOat 90**, Flour | 125 | 26.59 |
| Blank | 171 | N/A‡ |

Figure 3:
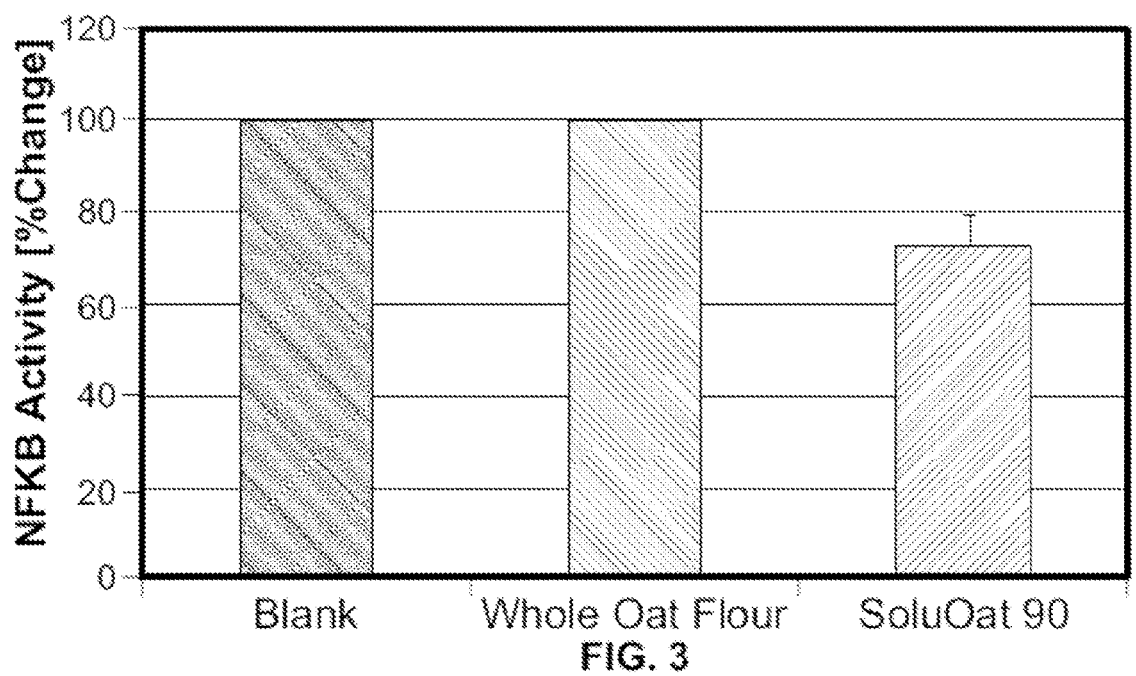
FIG. 3 depicts the percent change in NF-κB inhibition activity among whole oat flour, the methods described herein ("SoluOats"), and a blank.

*% inhibition was calculated against blank reading
**SoluOat 90 denotes that 90% of SoluOat was whole oat flour
†All samples were tested at concentration of 2 mg/mL
‡Not applicable FIG. 3 illustrates the percent of NF-κB inhibition in the samples.

Example 2

SoluOat flour and whole oat flour were produced in a traditional roller mill creating 150 micron of average particle size. The SoluOat flour was applied to various types of foods and beverages. The applications included instant flour application, dry ingredient in baking and yogurt processing, and ready-to-drink (RTD) beverage applications. A grainy texture was observed in some finished product applications containing the SoluOats. It was believed that the particle size of the SoluOat flour was the main driver for the grainy texture observed. As used herein "SoluOat," "SoluOat flour," "SoluOat 90" or "regular SoluOat," whether singular or plural, shall mean 90% whole oat flour 5% sugar, 4.5% maltodextrin and 0.5% mixed tocopherol made in accordance with the methods set forth in the present disclosure.

Milled SoluOat flour was micronized using a Fluid Energy Micro-Jet Series 8 mill (jet mill) with a sock installed on the discharge to collect the milled (micronized) flour. A Brabender volumetric screw feeder with a 1" diameter helical screw metered the feed material into the mill. Operating conditions of the jet mill are shown in the table below:

| Material | Feed Rate, lb/hr |
|---|---|
| SoluOat flour | 10 |
| SoluOat 100 flour | 10 |
| Whole Oat Flour | NA |

Figure 5:
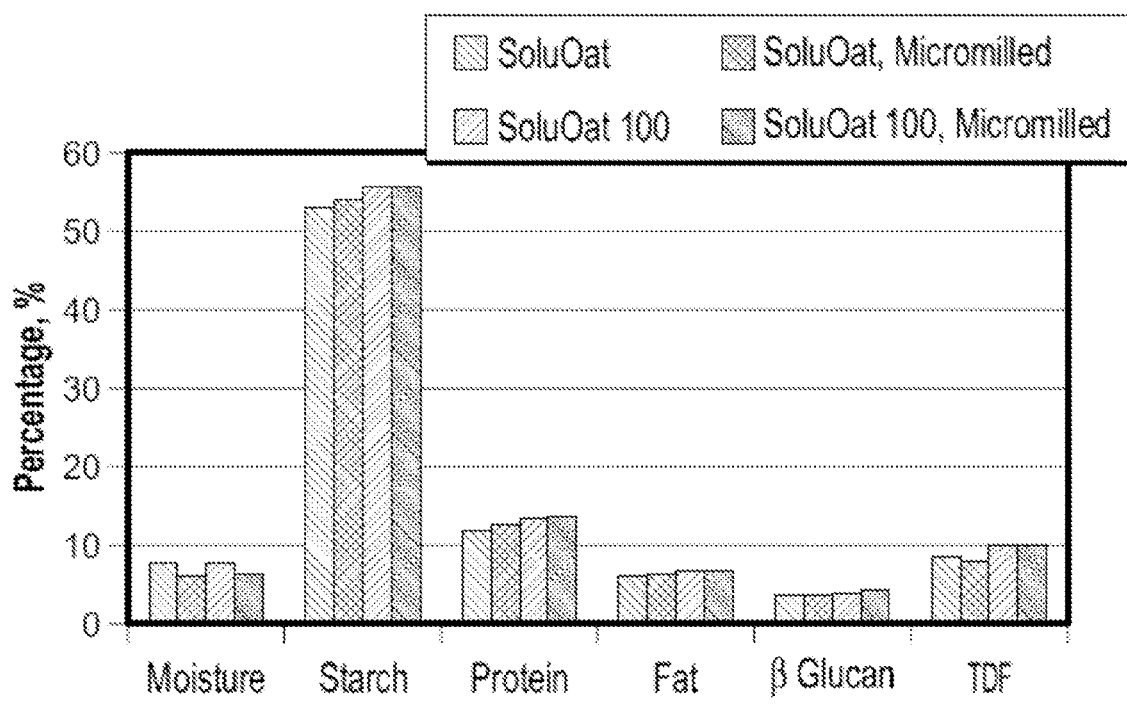
FIG. 5 depicts the percent of moisture, starch, protein, fat, B-glucan and TDF included in SoluOats, SoluOat 100, SoluOat, mircomilled and SoluOat 100 micromilled.

Chemistry analyses of the SoluOat flours before and after the jet mill process were conducted, and the impact of the jet mill process on viscosity and particle size were analyzed. The micro-milling process did not affect the nutrient composition of the SoluOat flours. A reduction of moisture in micronized SoluOat flours was noticed, likely due to high volume of air flow during processing. The table below, as well as FIG. 5, shows the proximate composition of SoluOat flours. As used herein, "SoluOat," "SoluOat flour," "SoluOat 90" or "regular SoluOat," whether singular or plural, shall mean 90% whole oat flour 5% sugar, 4.5% maltodextrin and 0.5% mixed tocopherol made in accordance with the methods set forth in the present disclosure. "SoluOat 100," whether singular or plural, shall mean 99.5% whole oat flour and 0.5% mixed tocopherol made in accordance with the methods set forth in the present disclosure.

| Description | Moisture, % | Starch, % | Protein, % | Fat, % | β Glucan, % | Total Dietary Fiber (TDF), % |
|---|---|---|---|---|---|---|
| SoluOat flour | 7.68 | 53.00 | 11.81 | 6.11 | 3.59 | 8.56 |
| SoluOat flour, micronized | 6.04 | 54.21 | 12.64 | 6.38 | 3.54 | 7.97 |
| SoluOat 100 flour | 7.86 | 55.71 | 13.71 | 6.71 | 3.91 | 9.91 |
| SoluOat 100 flour, micronized | 6.39 | 55.78 | 13.86 | 6.83 | 4.28 | 9.71 |

The particle size of SoluOat flours was measured by Malvern particle size analysis. In the table below, mean particle size in micron (μm) for a sample was from a volume basis. The d(0,1), d(0,5) and d(0,9) values represent the largest particle size for the $10^{th}$, $50^{th}$ and $90^{th}$ percentiles respectively. This means that for SoluOat flour, 10% of the particles are 104 microns or less, 50% are 190 microns or less, and 90% are 317 microns or less. The mean particle size of the SoluOat flour was reduced from 200 micron to 46 micron and that of SoluOat 100 was reduced from 282 micron to 89 micron. Thus, the jet mill process was found to be effective to reduce particle size for SoluOat flours.

| Sample Description | Mean particle size (μm) | d (0.1) | d (0.5) | d (0.9) |
|---|---|---|---|---|
| SoluOat | 200 | 104 | 190 | 317 |
| SoluOat micronized | 46 | 4 | 17 | 147 |
| SoluOat 100 | 282 | 126 | 262 | 477 |
| SoluOat 100 micronized | 89 | 6 | 31 | 260 |
| Whole oat flour | 305 | 15 | 277 | 668 |
| Whole oat flour, micronized | 105 | 6 | 31 | 348 |

Figure 6:
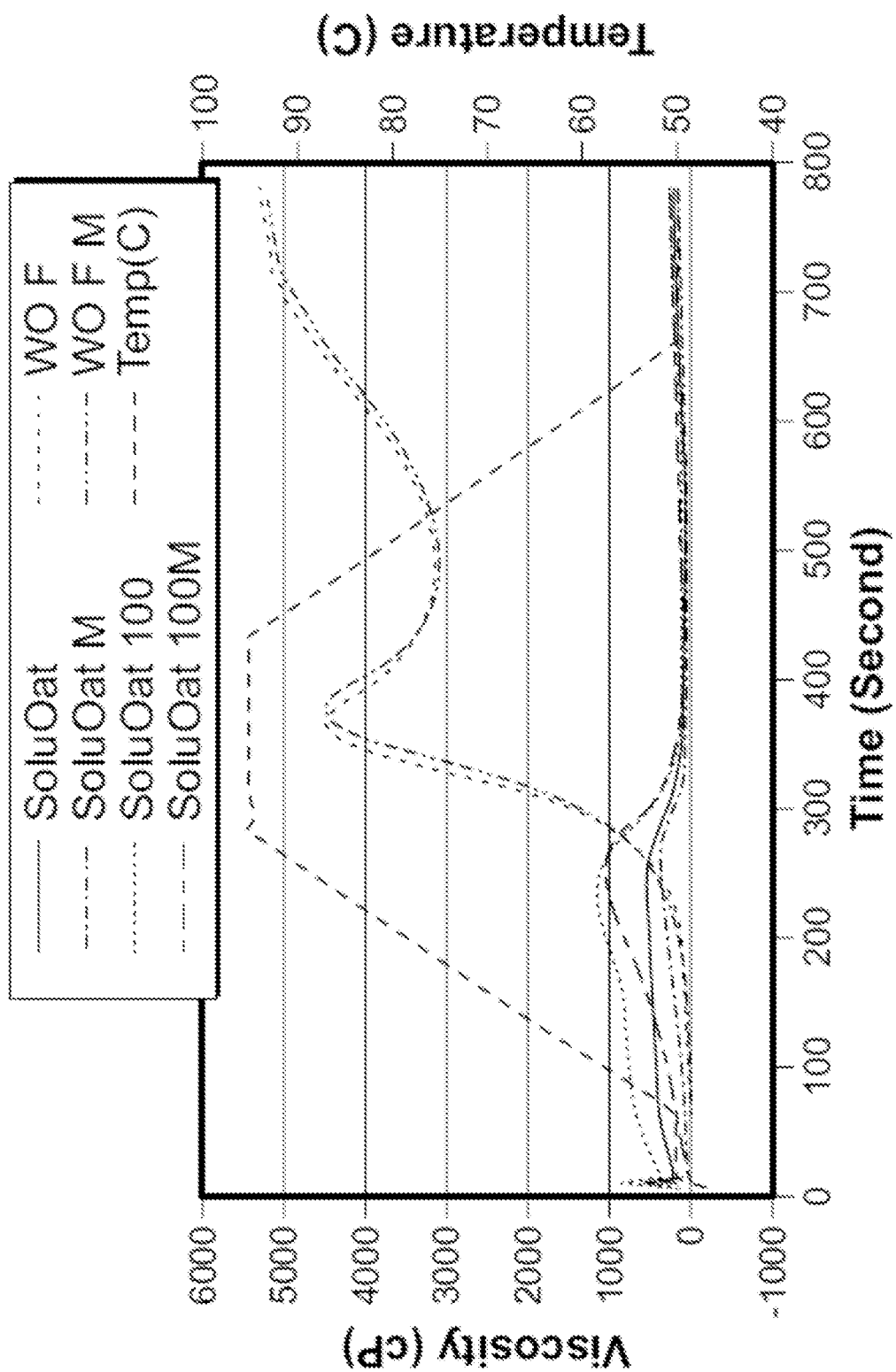
FIG. 6 depicts the viscosity of oat flour made in accordance with various aspects of the present disclosure compared to non-hydrolyzed whole oat flour or whole oat flour that is micro milled.

The viscosity of the jet-milled soluble oat flours made in accordance with the present disclosure was also assessed. FIG. 6 depicts a viscosity profile for soluble oat flours and whole oat flours before and after the jet milling process. Maximum, final, and minimum viscosities are provided in the table below. Maximum viscosity of micronized soluble oat flours (SoluOat and SoluOat 100) was reduced about 10% compared to non-micronized SoluOat flour and SoluOat 100 flour. However, the final viscosity and minimum viscosity of micronized soluble oat flours (SoluOat and SoluOat 100) were similar to un-micronized soluble oat flour (SoluOat and SoluOat 100) samples. In the legend of FIG. 6 "M" denotes "micronized" and "WOF" denotes "whole oat flour."

The table below identifies the RVA viscosity for SoluOat flours (SoluOat and SoluOat 100) (made using a standard milling process) before and after the micronization process set forth in certain aspects of the present disclosure.

| | Max Viscosity (0-8 min) | Final Viscosity | Min Viscosity (5-10 min) |
|---|---|---|---|
| SoluOat | 586 | 192 | 75 |
| SoluOat micronized | 418 | 188 | 66 |
| SoluOat 100 | 1158 | 254 | 85 |
| SoluOat 100 micronized | 1051 | 269 | 86 |
| Whole oat flour | 4492 | 5296 | 1435 |
| Whole oat flour, micronized | 4486 | 5240 | 1318 |

The following formulas are formulas for yogurt products containing soluble oat flour made in accordance with the present disclosure and using a standard milling process, herein referred to as "SoluOat" and the flour made in accordance with the micronization process, herein referred to as "SoluOat M."

| Ingredient | SoluOat, % | SoluOat M*, % |
|---|---|---|
| Skim milk | 78.03 | 78.03 |
| Cream 36% Fat | 2.29 | 2.29 |
| Non-Fat Dry Milk | 0.5 | 0.5 |
| Milk Protein Concentrate | 3.24 | 3.24 |
| Corn Starch | 0.63 | 0.63 |
| SoluOats | 5.29 | 0 |
| SoluOats, micronized | 0 | 5.29 |
| Mixed Berry Fruit Prep | 10 | 10 |
| Potassium Sorbate | 0.02 | 0.02 |

Yogurt products containing soluble oat flour were produced as follows. Dry ingredients, including the SoluOat flour, were dispersed into skim milk at 50° F. using a paddle blender. Cream was added to adjust the fat content. The mixed milk fluids were subjected to homogenization process at 750/2500 PSI pressure at 130-140° F., followed by heat treatment at 200° F. for 5 minutes. The fluid milks were inoculated with a culture at 110° F. Finally, the product was cooled to 68° F. for packaging and cold storage.

Sensory analysis conducted on the yogurt product indicated that the product with micronized SoluOat showed smoother texture than product containing non-micronized SoluOat flour. Mouthfeel of yogurt products between non-micronized and micronized SoluOats were different. Furthermore, the product with micronized SoluOat exhibited a drier texture than the product containing non-micronized SoluOat flour.

The following table includes formulas for juice products with SoluOat and SoluOat M* (micronized SoluOat flour):

| Ingredient | SoluOat, % | SoluOat M*, % |
|---|---|---|
| Apple juice | 54.1 | 54.1 |
| Water | 34.8 | 34.8 |
| Sugar | 3.7 | 3.7 |
| SoluOat | 3.5 | 0 |
| SoluOat 100 | 0 | 3.5 |
| Orange Juice Concentrate | 3.1 | 3.1 |
| Strawberry Juice Conc. | 0.2 | 0.2 |
| Citric acid | 0.2 | 0.2 |
| Beta Carotene | 0.2 | 0.2 |
| CMC gum | 0.1 | 0.1 |
| Gellan gum | 0.025 | 0.025 |
| Strawberry flavor | 0.085 | 0.085 |

*SoluOat M: SoluOat, micronized.

Juice products containing SoluOat flour were produced in a microthermic process unit. Gums (CMC and gellan gum) were dispersed in water at ambient temperature using a high shear mixer for 5 minutes. SoluOat flours were hydrated in apple juice at ambient condition using a gentle paddle mixer for 45 minutes. The SoluOat and apple juice slurry was subsequently added into the gum dispersion. The remaining ingredients were added to the SoluOat/gum solution using a high shear mixer. The mixed batch was thermally processed, for example, by using a tubular heat exchanger and a homogenization process.

Sensory evaluation was conducted for the products made with non-micronized SoluOat flour and with micronized SoluOat flour. A smooth texture for the product with micronized SoluOat was observed. In addition, the product with micronized SoluOat exhibited less grain flavor and a different flavor profile than the SoluOat flour made using standard milling procedures. In particular, GC-MS analysis of micronized SoluOat in full scan mode exhibited selective volatile compound losses, approximately 30%. The volatile compounds included 2,4-dimethyl-1-heptene, α-pinene, 1,3,5-trimethyl benzene and undecane.

In summary, the micronization process maintained the whole grain status of SoluOat flour during processing. The reduced particle size provided smoother texture in semi-solid and beverage product applications. The flavor differences observed for micronized flours are believed to be caused by the stripping of grain flavor with the high volumetric flow of compressed air used in the jet mill micronizing process.

Example 3

Samples for RVA/viscosity testing were prepared by grinding samples to pass a 60 mesh sieve. A 3.44 gram sample at dry weight basis was measured and transferred to a sample pan. Deionized water was added to the sample for a total weight of 29 grams.

In accordance with the testing procedure, a sample of the soluble oat flour was stirred at 960 rpm for the first 10 seconds, and the stirring was reduced to 160 rpm during testing. The initial temperature of the sample was maintained at 50° C. for 1 minute and the temperature was increased to 95° C. for 3 minutes 45 seconds. The sample was held at 95° C. for 2 minute and 30 seconds and was cooled down to 50° C. for 3 minutes 45 seconds and test was complete after a 2 minute hold.

Peak viscosity of the samples is shown in the tables below. In particular, maximum viscosity was identified between 0 to 8 minutes and minimum viscosity between 5 to 10 minutes. Final viscosity was identified at the completion of the cooling stage of the RVA test.

RVA test results of extruded oat flour before and after extrusion process with enzyme treatment are shown below. As used herein "SoluOat," "SoluOat flour," "SoluOat 90" or "regular SoluOat," whether singular or plural, shall mean 90% whole oat flour 5% sugar, 4.5% maltodextrin and 0.5% mixed tocopherol made in accordance with the methods set forth in the present disclosure. "SoluOat 100," whether singular or plural, shall mean 99.5% whole oat flour and 0.5% mixed tocopherol made in accordance with the methods set forth in the present disclosure.

| | Wet Mix % | % | RVA Viscosity (cP) | | |
|---|---|---|---|---|---|
| Description | Moisture | Enzyme | Peak | Min | Final |
| Raw Oat Flour | — | 0.0000 | 2,768 | 1,874 | 3,573 |
| Extruded Oat Flour | 29 | 0.0000 | 1,262 | 895 | 2,215 |
| SoluOat 90 | 29 | 0.0675 | 301 | 65 | 160 |
| Raw Oat Flour | — | 0.0000 | 4,717 | 1,349 | 5,282 |
| Extruded Oat Flour | 32 | 0.0000 | 2,801 | 226 | 487 |
| SoluOat 100 | 32 | 0.1200 | 540 | 58 | 161 |

Viscosity reduction of hydrolyzed, extruded oat flour made in accordance with the present disclosure ("SoluOat"), flour made using only extrusion (no enzyme) and raw oat flour (no extrusion or enzyme).

| Description | Wet Mix % Moisture | % Enzyme | % reduction in viscosity | | |
|---|---|---|---|---|---|
| | | | Peak | Min | Final |
| Raw Oat Flour | — | 0.0000 | 0 | 0 | 0 |
| Extruded Oat Flour | 29 | 0.0000 | 54.4 | 52.2 | 38.0 |
| SoluOat 90 | 29 | 0.0675 | 89.1 | 96.5 | 95.5 |
| Raw Oat Flour | — | 0.0000 | 0 | 0 | 0 |
| Extruded Oat Flour | 32 | 0.0000 | 40.6 | 83.2 | 90.8 |
| SoluOat 100 | 32 | 0.1200 | 88.6 | 95.7 | 97.0 |

In accordance with the viscosity testing, dry mix for SoluOat 90 contained 90% whole oat flour, 5% sugar, 4.5% maltodextrin and 0.5% mixed tocopherol. Enzyme was added to the dry mix at the level of 0.075% of whole oat flour. The dry mix for SoluOat 100 contained 99.5% whole oat flour with 0.5% mixed tocopherol. The enzyme for SoluOat 100 was added to dry mix at the level of 0.12% of whole oat flour. Peak viscosity of raw oat flour varied from 2,800 to 4,700 cP. Approximately 40% to 55% reduction of peak viscosity was achieved by extrusion process only at the same level of moisture and mechanical energy. However, about 90% reduction of peak viscosity was achieved by the extrusion process with enzyme treatment.

The invention may be embodied in other specific forms without departing from the spirit or essential characteristics thereof. The foregoing embodiments, therefore, are to be considered in all respects illustrative rather than limited the invention described herein. Scope of the invention is thus indicated by the appended claims, rather than by the foreign description, and all changes that come within the meaning and range of equivalency of the claims are intended to be embraced therein.

What is claimed is:

1. A composition comprising whole grain oat flour wherein the whole grain oat flour meets the standard of identity for whole grain and wherein the composition disperses in less than about 5 seconds in a liquid media at 25° C. wherein the whole grain oat flour contains about 20-35% more avenanthramides on a weight basis compared to native whole grain oat flour.

2. The composition of claim 1 further comprising sugar.

3. The composition of claim 1 wherein the composition contains 99.5 wt % whole grain oat flour and 0.5 wt % tocopherols.

4. The composition of claim 1 wherein the composition contains 90 wt % whole grain oat flour, 5 wt % sugar, 4.5 wt % maltodextrin and 0.5 wt % mixed tocopherols.

5. The composition of claim 1 wherein the starchy endosperm, germ and bran of the whole grain oat flour are present in the same relative proportions as they exist in the intact whole grain oat.

6. The composition of claim 1 wherein the avenanthramide content of the whole grain oat flour is about 35% greater on a weight basis than the avenanthramide content of native whole grain out flour.

7. The composition of claim 1 wherein the whole grain oat flour exhibits nuclear factor-kappa B inhibition activity wherein the nuclear factor-kappa B inhibition activity is at least about 25% greater than the nuclear factor-kappa B inhibition activity of native whole grain oat flour.

8. A composition comprising whole grain oat flour, wherein the whole grain oat flour contains about 20-35% more avenanthramides on a weight basis compared to native whole grain oat flour.

9. The composition of claim 8 wherein the avenanthramide content of the whole grain oat flour is about 35% greater on a weight basis than the avenanthramide content of native whole grain out flour.

10. The composition of claim 8 wherein the whole grain oat flour exhibits nuclear factor-kappa B inhibition activity wherein the nuclear factor-kappa B inhibition activity is at least about 25% greater than the nuclear factor-kappa B inhibition activity of native whole grain oat flour.

11. A composition produced using the following process:
  a. combining a whole grain oat flour starting mixture with an aqueous enzyme solution to form an enzyme starting mixture having a moisture content of 25 to 40 wt %;
  b. heating the enzyme starting mixture to between about 120° F. and 200° F.;
  c. adding the heated starting mixture to an extruder and extruding the mixture until the temperature of the mixture increases to about 260° F. to 300° F. wherein the enzyme is deactivated to form the composition, wherein the composition comprises whole grain oat flour;
  wherein the whole grain oat flour maintains its standard of identity throughout processing and the composition disperses in less than about 5 seconds in a liquid media at 25° C. and the whole grain oat flour contains at least 20% higher level of avenanthramides on a weight basis compared to native whole grain oat flour.

12. The composition of claim 11 wherein the avenanthramide content of the whole grain oat flour is about 35% greater on a weight basis than the avenanthramide content of native whole grain oat flour.

13. The composition of claim 11 wherein the whole grain oat flour exhibits nuclear factor-kappa B inhibition activity wherein the nuclear factor-kappa B inhibition activity is at least about 25% greater than the nuclear factor-kappa B inhibition activity of native whole grain oat flour.

14. The composition of claim 11 wherein the enzyme is a-amylase.

15. The composition of claim 11 wherein the enzyme starting mixture comprises 0.01-0.5 wt % a-amylase.

16. The composition of claim 11 wherein the enzyme starting mixture comprises about 0.15 wt % a-amylase.

17. The composition of claim 11 wherein the starting mixture further comprises sugar.

18. The composition of claim 11 wherein the starting mixture further comprises mixed tocopherols.

19. The composition of claim 11 wherein the moisture content of the enzyme starting mixture in the extruder is about 28-32 wt %.

20. The composition of claim 11 wherein, after deactivation of the enzyme, the composition exits the extruder.

21. The composition of claim 11 further comprising pelletizing the extruded mixture and granulating the pelletized mixture to form the composition.

22. The composition of claim 11 further comprising milling the extruded mixture to create ultrafine particles having a size of about 10-50 microns.

23. The composition of claim 11 further comprising milling the extruded mixture to create ultrafine particles having a size of about 10-450 microns.

24. The composition of claim 2 further comprising maltodextrin.

25. The composition of claim 17 wherein the starting mixture further comprises maltodextrin.

26. The composition of claim 1, wherein the liquid media is water.

27. The composition of claim 11, wherein the liquid media is water.

* * * * *